US00PP15097P2

(12) United States Plant Patent
Boeder

(10) Patent No.: US PP15,097 P2
(45) Date of Patent: Aug. 24, 2004

(54) CHRYSANTHEMUM PLANT NAMED 'BRILLIANT YELLOW'

(50) Latin Name: *Chrysanthemum morifolium*
Varietal Denomination: Brilliant Yellow

(75) Inventor: Mark Roland Boeder, The Hague (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 10/426,845
(22) Filed: May 1, 2003
(51) Int. Cl.[7] ..... A01H 5/00
(52) U.S. Cl. ..... Plt./295
(58) Field of Search ..... Plt./295

*Primary Examiner*—Anne Marie Grunberg
(74) *Attorney, Agent, or Firm*—Parkhurst & Wendel, L.L.P.

(57) ABSTRACT

A Chrysanthemum plant named 'Brilliant Yellow' characterized by its pyramidal shaped inflorescence, medium sized blooms with yellow ray-florets and green disc florets.

3 Drawing Sheets

Related cultivars: 'Brilliant Yellow' is a new type of chrysanthemum plant unrelated to any in US patented plant cultivars.

BACKGROUND OF THE INVENTION

'Brilliant Yellow' is a product of a breeding-program which had the objective of creating new chrysanthemum cultivars with a pyramidal shaped inflorescence with a daisy type flower and a 7 week response. The new plant of the present invention comprises a new and distinct cultivar of Chrysanthemum plant. 'Brilliant Yellow' is a seedling from a cross in a breeding program maintained under the control of inventor. The female parent is an unnamed seedling not available to inventor for description. The male parent is unknown, being a mixed population of a group of male parents. The new and distinct cultivar was discovered and selected as a flowering plant within the progeny of the stated cross by Mark Roland Boeder in a controlled environment (greenhouse) in Rijsenhout Holland in 2001. The first act of asexual reproduction of 'Brilliant Yellow' was accomplished when vegetative cuttings were taken from the initial selection in 2001 in a controlled environment in Rijsenhout Holland.

SUMMARY OF THE INVENTION

The present invention is a new and distinct variety of chrysanthemum with a pyramidal inflorescence, bearing medium sized blooms with yellow ray-florets and green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
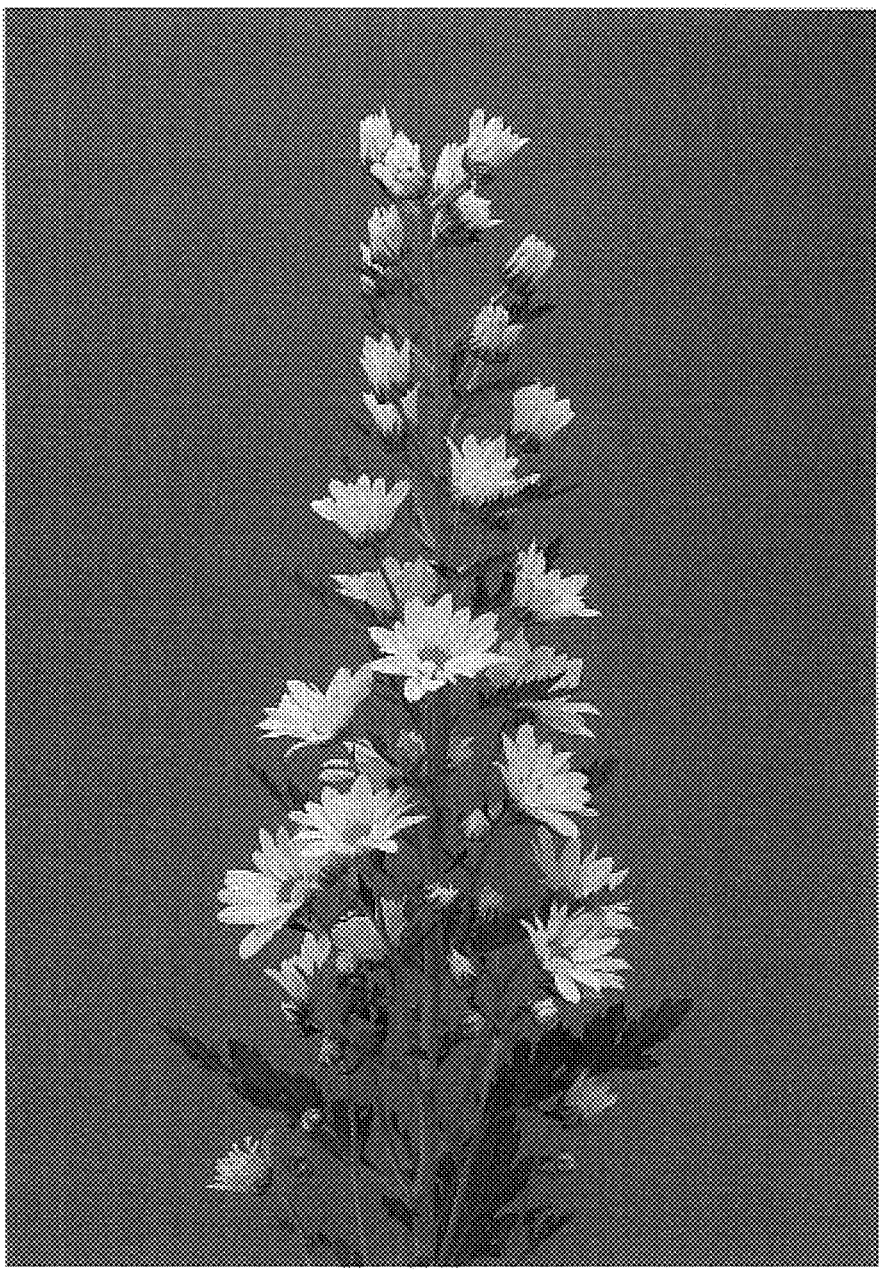
FIG. 1 shows a plant of the cultivar in full bloom.
Figure 2:
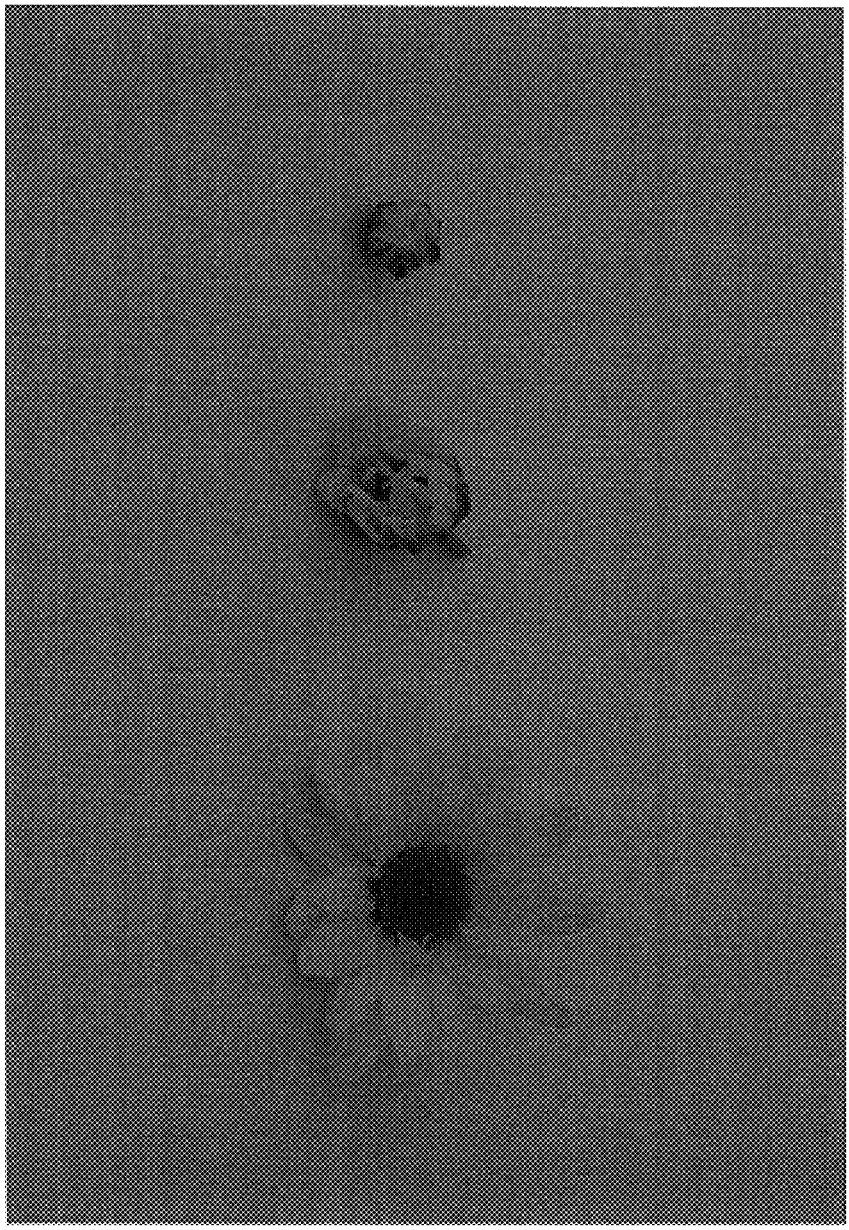
FIG. 2 shows the various stages of bloom of the new cultivar.
Figure 3:
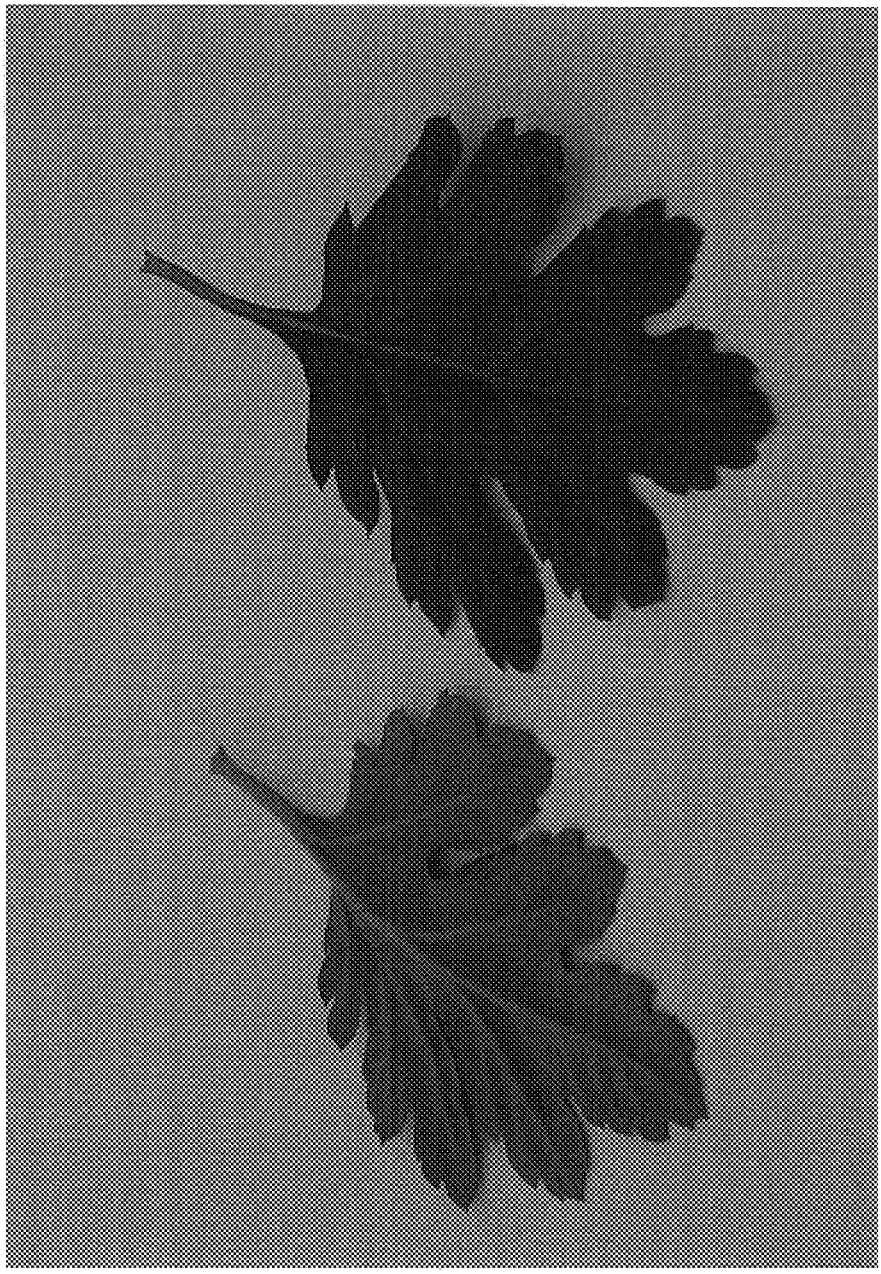
FIG. 3 shows the foliage of the new cultivar.

This new variety of chrysanthemum is of the botanical classification Chrysanthemum morifolium. The observations and measurements were gathered from plants grown in April–May in a greenhouse in Rijsenhout Holland in a photo-periodic controlled crop under conditions generally used in commercial practice. The greenhouse temperatures during this crop were at day-time between 18° C. and 25° C. and at night 20° C. After a long day period of 21days the photo-periodic response time in this crop was 47 days. During the long day period retardants were applied 2 times in an average dose of 2 gram/liter water. The plants were observed (directly) during the flowering of this crop. In the vegetative stage, this chrysanthemum plant is partially resistant to infestation by Western flower thrips. The plants are not tolerant to low night temperatures. This new variety produces pyramidal shaped inflorescences, flowering from bottom to top, bearing medium sized blooms consisting of yellow ray-florets and green disc-florets blooming on the plant for 5 weeks. This new variety of chrysanthemum has been found to retain its distinctive characteristics throughout successive propagations however the phenotype may vary significantly with variations in environment such as light intensity and temperature. 'Brilliant Yellow' can be planted with assimilation lightning (high pressure sodium lamps) between week 28 and week 18 under greenhouse conditions in Holland.

From the cultivars known to inventor the most similar existing cultivar in comparison to 'Brilliant Yellow' is Yellow Reagan (U.S. Plant Pat. No. 8,884). When 'Yellow Reagan' and 'Brilliant Yellow' are being compared the following differences and similarities are noticed: The differences of 'Yellow Reagan' and 'Brilliant Yellow' are (1) Inflorescence shape, (2) Long day treatment and (3) Flowering response. (1) Inflorescence shape. The shape of 'Yellow Reagan' is corymbiform and that of 'Brilliant Yellow' strongly pyramidal, unlike any existing chrysanthemum cultivars; (2) Long day treatment. In the cultivation of 'Yellow Reagan' a long day treatment, with more than 13 hr light, of 14 days is needed, while for 'Brilliant Yellow' 21 long days are required; (3) Flowering response. The response of 'Yellow Reagan' is 51 days, while that of 'Brilliant Yellow' is 47 days.

The following is a description of the plant and characteristics that distinguish 'Brilliant Yellow' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of Cultivar 'Brilliant Yellow'.

Bud:
*Size.*—Medium, cross-section 0.8 cm height 0.5 cm.
*Outside color.*—Green 138 B.
*Involucral bracts.*—2 rows, length 7 mm, width 3 mm.
*Involucral bracts among disc-florets.*—Not present.
*Involucral bracts color.*—Green 137 A.

Bloom:
*Shape inflorescence.*—Pyramidal.
*Height inflorescence.*—30 cm.
*Type bloom.*—Daisy.
*Size bloom.*—Medium.
*Fully expanded.*—5–6 cm.
*Number of blooms per stem.*—Average of 25.
*Performance on the plant.*—5 weeks.
*Seeds* (*if crossed*).—Produced in large quantities, oval shaped, Greyed-brown 199A, 2 mm in length.
*Fragrance.*—Typical chrysanthemum, slight. Near the top 1 cm, near.
*Peduncle length.*—The middle 3 cm, near the bottom 7 cm.
*Peduncle color.*—Green 137C.

Color:
*Center of the flower* (*disc-florets*).—Immature Yellow-Green 145 A. Mature Yellow 13 A.
*Color of upper surface of the ray-florets.*—Yellow 3 A.
*Color of the lower surface of the ray-florets.*—Yellow 4 A.
*Tonality from distance.*—A spray mum with yellow flowers and a green disc.
*Color of the upper surface of the ray-florets after aging of the plant.*—Yellow 3 A.

Ray florets:
*Texture.*—Upper and under side smooth.
*Number.*—22–24.
*Cross-section.*—Flat.
*Longitudinal axis of majority.*—Straight.
*Length of corolla tube.*—0.3–0.4 cm.
*Ray-floret margin.*—Entire.
*Ray-floret length.*—2.5 cm.
*Ray-floret width.*—0.9 cm.
*Ratio length/width.*—3.
*Shape of tip.*—Pointed.

Disc florets:
*Disc diameter.*—1.2 cm.
*Distribution of disc florets.*—Numerous, clearly visible at all stages of flowering.
*Shape.*—Tubular.
*Color.*—Yellow-green 145 A.
*Receptacle shape.*—Conical raised.

Reproductive organs:
*Stamen.*—Present in disc florets only.
*Stamen color.*—Yellow-orange 15 C.
*Pollen.*—Produced in large quantities.
*Pollen color.*—Yellow 13 A.
*Styles.*—Present in both ray and disc florets.
*Style color.*—Yellow 12 A.
*Style length.*—6 mm.
*Stigma color.*—Yellow-green 145 D.
*Stigma width.*—0.5 mm.
*Ovaries.*—Enclosed in florets.

Plant:
*Form.*—A spray mum meant for erect culture.
*Growth habit.*—Upright.
*Growth rate.*—Vigorous.
*Height.*—90 cm.
*Internode length.*—1.5–2 cm.
*Stem color.*—Green 137 C.
*Stem strength.*—Strong.
*Stem brittleness.*—Not brittle.
*Stem anthocyanin coloration.*—Absent.
*Flowering response* (*photo-periodic controlled crop, not natural season*).—47 days in Summer in the Netherlands.

Foliage:
*Color immature stage.*—Upper side Green 139 A. Under side Green 139 C.
*Color mature stage.*—Upper side Green 136 B. Under side Green 136 C.
*Color midvein.*—Upper side Green 138 C. Under side Green 139 D.
*Size.*—Medium; length 11–12 cm, width 7–8 cm.
*Quantity* (*number per single stem*).—35. Shape: Ovate. Texture Upper Side: Fleshy and glabrous. Texture Under Side: Pubescent. Venation Arrangement: Palmate. Shape of the Margin: Serrate. Shape of Base of Sinus Between Lateral Lobes: Rounded. Margin of Sinus Between Lateral Lobes: Diverging. Shape of Base: Rounded. Apex: Mucronulate Petiole Length: 2.5 cm. Petiole Color: Green 138 C.

TABLE 1

Differences with the comparison varieties

| | 'Brilliant Yellow' | 'Yellow Reagan' |
|---|---|---|
| Inflorescence shape | Strongly pyramidal | Corymbiform |
| Long day treatment | 21 days | 14 days |
| Flowering response | 47 days | 51 days |

I claim:

1. A new and distinct variety of chrysanthemum plant as described and illustrated.

* * * * *